United States Patent [19]

Gupton et al.

[11] Patent Number: 4,871,859

[45] Date of Patent: Oct. 3, 1989

[54] PROCESS FOR PREPARING PYRIDINE CARBOXYLIC ACID ESTERS

[75] Inventors: B. Franklin Gupton, Virginia Beach; James H. Rea, Portsmouth, both of Va.; Werner H. Mueller, East Greenwich, R.I.

[73] Assignee: Hoechst Celanese Corporation

[21] Appl. No.: 163,252

[22] Filed: Mar. 2, 1988

[51] Int. Cl.$^4$ .................. C07D 213/08; C07D 211/78
[52] U.S. Cl. .................................... 546/250; 546/321
[58] Field of Search ................................ 546/250, 321

[56] References Cited

U.S. PATENT DOCUMENTS 4,169,951  10/1979  Beschke et al. ...................... 546/250
4,723,011   2/1988  Doehner, Jr. ....................... 546/250

OTHER PUBLICATIONS

Bouvier, Bull. et al, Soc. Chim. Fr., pp. 711–712, (1986).

Primary Examiner—Mary C. Lee
Assistant Examiner—Robert C. Whittenbaugh
Attorney, Agent, or Firm—Depaoli & O'Brien

[57] ABSTRACT

A novel method is disclosed for the preparation of 2,3-pyridine-dicarboxylates by the reaction of a ketoester such as dimethyl oxalacetate with an α,β-unsaturated aldehyde or ketone such as 2-ethylacrolein and at least 1 molar equivalent of ammonium salt in suitable solvent utilizing a dehydrogenation catalyst such as palladium on carbon.

15 Claims, No Drawings

PROCESS FOR PREPARING PYRIDINE CARBOXYLIC ACID ESTERS

BACKGROUND OF THE INVENTION

Literature methods for preparing 5,6-dialkyl and 5,6-alkyl-arylpyridine-2,3-dicarboxylic acids and esters are limited and often require oxidation of alkyl or aryl substituents at positions 2 and 3 in order to obtain diacids. Recently there has been disclosed a method for the preparation of substituted and disubstituted pyridine-2,3-dicarboxylic acid esters and 2-alkyl nicotinates utilizing α-halo-β-ketoesters and α,β-unsaturated aldehydes or ketones in the presence of an ammonium salt. The use of α-halo-β-ketoesters is not desired due to the fact that such materials are usually costly and unstable.

DESCRIPTION OF THE PRIOR ART

The most pertinent prior art is European Patent Application No. 220518 which was published on May 6, 1987. This published European Patent Application is assigned to American Cyanamid Company and on the face thereof indicates that priority is based on a U.S. application Ser. No. 791,671, filed Oct. 28, 1985 now U.S. Pat. No. 4,723,011.

The European Patent Application discloses preparation of substituted and disubstituted pyridine-2,3-dicarboxylates by the reaction of an α-halo-β-ketoester such as chloro-diethyloxalacetate (chloro-DOX) and an α,β-unsaturated aldehyde or ketone such as 2-ethyl acrolein in the presence of at least 2 molar equivalents of an ammonium salt in order to produce the desired compunds.

Although the method disclosed in the above-identified European Patent Application is effective, nevertheless, because of the commercial importance of the compounds, particularly as useful intermediates for the preparation of herbicidal 2-(2-imidazolin-2-yl) nicotinic acids, esters and salts, any improvement in the process is of tremendous potential economic significance.

One disadvantage in using the method of said published European Patent Application is the fact that a halo-substituted ketoester is a more expensive starting material and the most common, namely chloro-DOX, is also not as stable as the non-halo-detoesters, i.e., DOX. Another disadvantage to this process is the formation of chloride salts, which leads to waste water disposal problems and requires the use of significantly more expensive materials of construction.

SUMMARY OF THE INVENTION

It has now been found that substituted and disubstituted pyridine carboxylic acid esters, such as pyridine-2,3-dicarboxylic acid esters, can be prepared by the reaction of a β-ketoester, such as DOX, with an α,β-unsaturated aldehyde or detone, such as 2-ethyl acrolein, in the presence of at least 1 molar equivalent of an ammonium salt utilizing a dehydrogenation catalyst or other hydrogen acceptor. It should be immediately apparent that the reaction mechanism involved in the instant invention is different from the reaction mechanism involved in the process of European Patent application No. 220518.

As disclosed in said European Patent Application 220518, the entire disclosure of which is incorporated by reference, pyridine-2,3-carboxylates are useful intermediates for the preparation of herbicidal 2-(2-imidazolin-2-yl) nicotinic acids, esters and salts such as those disclosed in European Patent Application No. 81103638.3, filed Dec. 1, 1981, as illustrated in the following diagram:

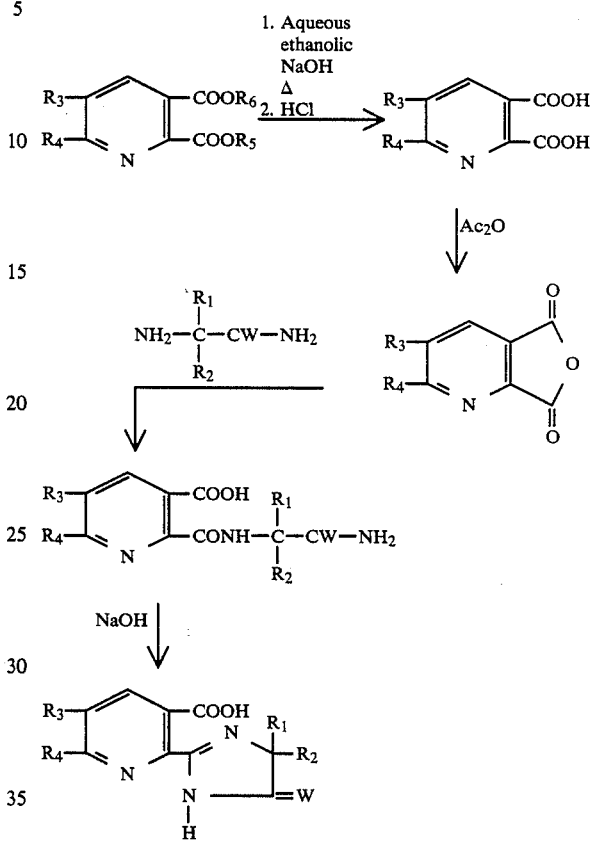

wherein $R_1$ is $C_1$–$C_4$ alkyl; $R_2$ is $C_1$–$C_4$ alkyl or $C_2$–$C_6$ cycloalkyl; and when $R_1$ and $R_2$ are taken together with the carbon to which they are attached they may represent $C_2$–$C_6$ cycloalkyl optionally substituted with methyl; W is O or S; and $R_2$ and $R_4$ are hydrogen, halogen $C_1$–$C_6$ straight or branched alkyl, alkenyl, or phenyl optionally substituted; $R_3$ and $R_4$ are each $C_1$–$C_4$ alkyl.

It is an object of this invention to provide a method for the preparation of substituted and disubstituted pyridine-2,3-dicarboxylic acid esters and 2-alkyl nicotinates utilizing β-ketoesters and α,β-unsaturated aldehydes or ketones in the presence of an ammonium salt and a dehyrogenation catalyst.

The present invention is a novel method for the preparation of substituted and disubstituted pyridine 2,3-dicarboxylates of formula I

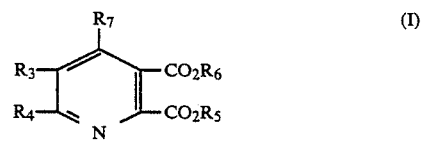

wherein $R_3$ is hydrogen, halogen, $C_1$–$C_6$ straight or branched alkyl, alkenyl, phenyl, or substituted-phenyl; $R_4$ and $R_7$ are each hydrogen, $C_1$–$C_6$ straight or branched alkyl, alkenyl, phenyl, or substituted-phenyl; $R_5$ and $R_6$ are each $C_1$–$C_4$ alkyl; comprising reacting a β-ketoester of formula II

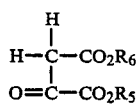

(II)

wherein $R_5$ and $R_6$ are defined above with an $\alpha,\beta$-unsaturated aldehyde or ketone of formula III

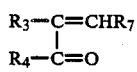

(III)

wherein $R_3$, $R_4$ and $R_7$ as described for in formula I above in the presence of a minimum of 1 molar equivalent of an ammonium salt in a solvent, utilizing a dehydrogenation catalyst and a temperature range of ambient temperature to the boiling point of the solvent until the reaction is essentially complete, as illustrated in the following reaction diagram:

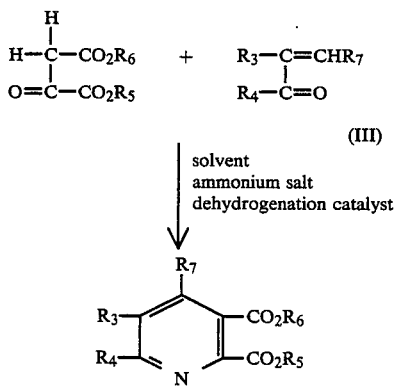

Solvents suitable for use in the method of this invention include: water, alcohols, chlorinated hydrocarbons, hydrocarbons, aromatic hydrocarbons, ethers, organic acids, esters, and aprotic solvents such as acetonitrile. The preferred solvents are lower alkyl alcohols, such as methanol, ethanol and propanol and aromatic hydrocarbons, such as benzene and toluene.

Thus, pyridine-2,3-dicarboxylic acid esters containing substituents in the 4-, 5- and 6-position may conveniently be prepared by admixing essentially equimolar amounts of a formula II ketoester and formula III $\alpha b,\beta$-unsaturated aldehyde or ketone with an ammonium salt in a suitable solvent, and stirring the resulting reaction mixture in the presence of a dehydrogenation catalyst at a temperature in the range of ambient temperature to the boiling point of the solvent, and preferably at reflux, until the reaction is essentially complete and isolating the formed 4-substituted, 4-5-disubstituted, 4,6-disubstituted, 5-substituted, 6-substituted or 5-6-disubstituted pyridine-2,3-dicarboxylic acid esters by standard laboratory techniques such as extraction, evaporation or column chromatography.

The amount of ammonium salt is not narrowly critical and amounts of from 1 to 3 mols of ammonium salt per mol of said aldehyde or ketone can be employed. Preferred ranges are 1-2 mols. It is to be understood that greater amounts of ammonium salts can be used, i.e., greater than 3 mols, but no advantage is gained.

The ammonium salts operable in the novel process of this invention are those which have sufficient solubility in the particular solvent employed. Examples include acetate, nitrate, sulfamate, chloride, sulfate, etc. Particularly preferred are the sulfamates and the acetates, especially when using low molecular weight alcohols as the solvent.

The dehydrogenation catalyst employed is conventional in the art and includes metals or compounds of platinum, palladium, ruthenium, iridium, nickel, iron, copper, antimony, cobalt, rhodium, etc. The dehydrogenation catalyst is usually used in a form of having the dehydrogenation metal or compound thereof deposited on a suitable support, such as alumina, carbon, clay, zeolites, chromia, zirconia, etc. A preferred dehydrogenation catalyst is palladium on carbon.

The mol ratio of the ester of formula II to the aldehyde or ketone of formula III is not narrowly critical and can range from 1:3 to 3:1. It is preferred to use 1:1 molar ratios.

Additionally, the method of the present invention is suitable for the preparation of substituted nicotinates of formula IV below

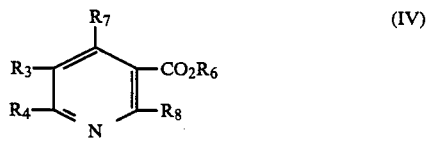

(IV)

wherein $R_3$, $R_4$, $R_6$ and $R_7$ are as described for formula I; and $R_8$ is $C_1$-$C_4$ alkyl; comprising reacting a $\beta$-ketoester of formula V

(V)

wherein $R_4$ and $R_6$ are as defined for formula IV above, with an $\alpha,\beta$-unsaturated aldehyde or ketone of formula III.

Formula IV nicotinates are also useful intermediates for the preparation of herbicidal 2-(2-imidazolin-2-yl) nicotinic acids, esters and salts by reaction with an aminocarboxamide in the presence of at least 3 equivalents of sulfur as described in U.S. Pat. No. 4,474,962 or by oxidation of $R_6$, for example, by the procedure described in U.S. Pat. No. 4,459,409, to yield the pyridine-2,3-dicarboxylic acid compounds of formula I above.

The following examples will illustrate the best mode contemplated for carrying out the novel process of this invention.

EXAMPLE I

To a 1 liter, 3-neck Morton flask fitted with a condenser, thermometer, heating mantle, magnetic stirrer and addition funnel is added 0.5 mols of ammonium acetate and 200 grams of toluene.

The mixture is heated to reflux (60°–110° C.) followed by the dropwise addition of 94.0 grams (0.5 mols) diethyl oxalacetate (DOX) over a 30-minute period. A 2.0 gram quantity of 5% palladium on carbon is then added tot he reaction mixture followed by the dropwise addition of 42.0 grams (0.5 mols) of freshly distilled 2-ethacrolein over 30 minutes.

The reaction temperature is maintained with stirring for approximately 2 hours followed by filtration of the catalyst and removal of the excess ammonium acetate if any. The solvent and lower boiling components are removed by evaporation, followed by vacuum distillation of the product at 180°–190° C. and 5 to 7 mm of mercury (absolute) in order to yield 34.7 wt. % of 5-ethylpyridine dicarboxylic acid, diethyl ester.

EXAMPLE 2

The procedure of Example 1 was repeated with the exception that 0.5 mols of ammonium acetate and 1.0 mols of acetic acid were utilized.

The yield of 5-ethylpyridine dicarboxylic acid diethyl ester was 47.2%.

EXAMPLE 3

The procedure of Example 1 was repeated with the exception that 289 grams of ethanol were used as the solvent as opposed to toluene.

The yield of 5-ethylpyridine dicarboxylic acid diethyl ester was 44.4%.

EXAMPLE 4

The procedure of Example 3 was repeated with the exception that 1.35 mols of ammonium sulfamate was employed instead of ammonium acetate.

The yield obtained was 50.5 wt. %.

EXAMPLE 5

The procedure of Example 4 was repeated with the exception that 289 grams of methanol were employed as opposed to 289 grams of ethanol. This example resulted in 47.3 wt. % of 5-ethylpyridine dicarboxylic acid diethyl ester.

EXAMPLE 6

The procedure of Example 5 was repeated with the exception that after the solvent and the lower boiling components have been removed by evaporation vacuum distillation was not carried out.

Instead toluene was added followed by acid extraction with a 20% HCL followed by pH adjustment to approximately 10 and back extraction with toluene. This procedure resulted in a yield of desired ester of about 48–49 wt. %.

It is to be understood that the order of additions of the reaction is not critical and they can all be added together at the beginning of the reaction with the dehydrogenation catalyst as opposed to the step-wise addition and the examples.

The procedure of Example 1 is repeated using the following in place of the DOX, and/or the 2-ethylacrolein.

TABLE

| EXAMPLE | ESTER | ALDEHYDE OR ESTER | PRODUCT |
| --- | --- | --- | --- |
| 7 | DOX | acrolein | pyridine-2,3-dicarboxylic acid, diethyl ester |
| 8 | DOX | 2-methylacrolein | 5-methylpyridine-2,3-dicarboxylic acid, diethyl ester |
| 9 | DOX | methyl vinylketone | 6-methylpyridine-2,3-dicarboxylic acid, diethyl ester |
| 10 | DOX | crotonaldehyde | 4-methylpyridine-2,3-dicarboxylic acid, diethyl ester |
| 11 | acetoacetic acid, ethyl ester | acrolein | 2-methylpyridine-3-carboxylic acid, ethyl ester |
| 12 | DOX | | |

TABLE-continued

| EXAMPLE | ESTER | ALDEHYDE OR ESTER | PRODUCT |
|---|---|---|---|
| | | | 6-phenylpyridine-2,3-dicarboxylic acid, diethyl ester |
| 13 | | | 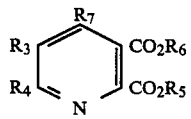 |
| | | | 2-phenylpyridine-3-carboxylic acid, ethyl ester |
| 14 | | | |
| | | | 2,6-diphenyl-3-carboxylic acid, ethyl ester |
| 15 | | | 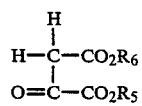 |
| | | | 2-phenyl-6-methylpyridine-3-carboxylic acid, ethyl ester |
| 16 | | | 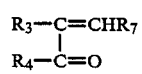 |
| | | | 6-phenyl-2-methyl-3-carboxylic acid, ethyl ester |

What is claimed is:

1. A method for the preparation of substituted and disubstituted pyridine-2-3-dicarboxylates of formula I:

$$R_3 \underset{R_4}{\overset{R_7}{\diagdown}} \underset{N}{\diagup} \overset{CO_2R_6}{\underset{CO_2R_5}{\diagdown}} \quad (I)$$

wherein $R_3$ is hydrogen, halogen, $C_1$–$C_6$ straight or branched alkyl, alkenyl, phenyl $R_4$ and $R_7$ are each hydrogen, $C_1$–$C_6$ straight or branched alkyl, alkenyl, phenyl, substituted-phenyl; and $R_5$ and $R_6$ are each $C_1$–$C_4$ alkyl; comprising reacting a β-ketoester of formula II;

$$\begin{array}{c} H \\ | \\ H-C-CO_2R_6 \\ | \\ O=C-CO_2R_5 \end{array} \quad (II)$$

wherein $R_5$ and $R_6$ are defined above with an α,β-unsaturated aldehyde or ketone of formula III:

$$\begin{array}{c} R_3-C=CHR_7 \\ | \\ R_4-C=O \end{array} \quad (III)$$

wherein $R_3$, $R_4$ and $R_7$ are as described in formula I in the presence of at least 1 molar equivalent of an ammomium salt in a solvent in the presence of a dehydrogenation catalyst and at a temperature range of ambient temperature to the boiling point of the solvent until the reaction is essentially complete.

2. A method according to claim 1 wherein the solvent is a lower alkyl alcohol.

3. The method of claim 2 wherein the solvent is methanol.

4. A method according to claim 2 wherein the ketoester is diethyl oxalacetate.

5. A method according to claim 1 wherein the aldehyde is 2-ethylacrolein.

6. A method according to claim 1 for the preparation of 5-substituted, 6-substituted and 5,6-disubstitited pyridine-2,3-dicarboxylic acid and esters.

7. A method according to claim 1 for the preparation of diethyl-5-ethylpyridine-2,3-dicarboxylate.

8. A method according to claim 1 for the preparation of diethyl 5-methylpyridine-2,3-dicarboxylate.

9. A method according to claim 1 for the preparation of diethyl-6-methylpyridine-2,3-dicarboxylate.

10. A method according to claim 1 for the preparation of diethyl-4-methylpyridine-2,3-dicarboxylate.

11. A method according to claim 1 for the preparation of diethyl-6-phenylpyridine-2,3-dicarboxylate.

12. A method according to claim 1 for the preparation of diethylpyridine-2,3-dicarboxylate.

13. A method for the preparation of substituted nicotinates having the structure:

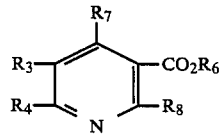

wherein $R_3$ is hydrogen, halogen, $C_1$–$C_6$ straight or branced alkyl, alkenyl, phenyl; $R_4$ and $R_7$ are each hydrogen, $C_1$–$C_6$ straight or branced alkyl, alkenyl, phenyl, substituted-phenyl; R$_6$ and R$_8$ are each C$_1$–C$_4$ alkyl; comprising reacting the ketoester of formula V:

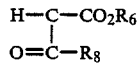

wherein R$_6$ and R$_8$ are as defined for formula IV, with an α,β-unsaturated aldehyde or ketone of formula III:

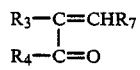

wherein R$_3$, R$_4$ and R$_7$ are as described in formula IV, in the presence of a minimum of 2 molar equivalents of an ammonium salt in an organic solvent in a temperature range of ambient temperature to the boiling point of the solvent until the reaction is essentially complete.

14. A method according to claim 10 for the preparation of 5-ethyl-2-methylnicotinate.

15. A method according to claim 10 for the preparation of ethyl-2-methyl-6-phenylnicotinate.